United States Patent [19]

Karamata et al.

[11] Patent Number: 4,797,279

[45] Date of Patent: Jan. 10, 1989

[54] INSECTICIDAL HYBRID BACTERIA FROM B.T. KURSTAKI AND B.T. TENEBRIONIS

[75] Inventors: Dimitri Karamata, Epalinges; Jean-Christophe Piot, Lausanne, both of Switzerland

[73] Assignee: Sandoz Ltd., Basel, Switzerland

[21] Appl. No.: 924,372

[22] Filed: Oct. 28, 1986

[30] Foreign Application Priority Data

Oct. 30, 1985 [GB] United Kingdom ............... 8526774

[51] Int. Cl.[4] .................... A61K 35/74; A01N 63/00; C12N 1/20
[52] U.S. Cl. ................................ 424/93; 435/252.31
[58] Field of Search ................ 435/253, 832, 172.2, 435/172.3; 424/93

[56] References Cited

U.S. PATENT DOCUMENTS 4,259,474  5/1981  Chakrabarty ................. 435/172

FOREIGN PATENT DOCUMENTS 0149162  7/1985  European Pat. Off. .

OTHER PUBLICATIONS

Gonzalez, Jose M., et al., Proc. Natl. Acad. Sci. U.S.A.,(22), pp. 6951–6955, 1982.
Kreig, A., et al., Anz Schaedlingsbekaempfung Umweltschutz 57(8) 145–150, 1984. Coden Aspucs Issn: 0340-7322.
Gonzalez and Carlton (Genetic Exchange), Genetic and Cellular Technology, vol. 1, pp. 85–95.
Battisti et al., J. Bacteriology, May 1985, vol. 162(2) pp. 543–550.
Fischer et al., Arch Microbio (1984) 139:213–217.
Lereclus et al., Mol. Gren. Genet.(1983) 191:307–13.
Klier et al., Mol. Gen. Genet.(1983) 191:257–262.
Macrina et al., Molecular Characterization Unique Deletion Mutants of Plasmid pAMB, Acedemic Press, 1980.

*Primary Examiner*—Blondel Hazel
*Attorney, Agent, or Firm*—Gerald D. Sharkin; Richard E. Vila

[57] ABSTRACT

The invention provides hybrid microorganisms comprising the gene coding for *b.t. kurstaki* delta-endotoxin and the gene coding for *b.t. tenebrionis* delta-endotoxin, their preparation, insecticidal compositions comprising such microorganisms and their use.

12 Claims, No Drawings

INSECTICIDAL HYBRID BACTERIA FROM B.T. KURSTAKI AND B.T. TENEBRIONIS

This invention relates to *Bacillus thuringiensis* (hereinafter B.t.) hybrids, their preparation, pesticidal compositions comprising such hybrids and their use.

More specifically, the invention relates to hybrid bacterial cells, comprising a plasmid with the gene coding for B.t. *kurstaki* delta-endotoxin and a plasmid with the gene coding for B.t. *tenebrionis* delta-endotoxin; they are obtainable by conjugation of an endotoxin crystal producing B.t. *kurstaki* strain and an endotoxin crystal producing B.t. *tenebrionis* strain and are capable of producing each of the delta-endotoxin crystals typical for a B.t. *kurstaki* strain and a B.t. *tenebrionis* strain. Delta-endotoxin crystals of B.t. *kurstaki* strains have a typical bipyramidal form. Delta-endotoxin crystals of B.t. *tenebrionis* are typically parallellipipedic (or cubic) in shape. The B.t. hybrids of the invention allow the biological control of the pests controlable by the B.t. *kurstaki* and B.t. *tenebrionis* parent strains.

The B.t. hybrids of the invention may be obtained in conventional manner by conjugation of a delta-endotoxin producing B.t. *kurstaki* strain and a delta-endotoxin producing B.t. *tenebrionis* strain, and isolation of the B.t. hybrids of the invention using isolation techniques known per se. Conjugation techniques are well known in the genetic engineering field (see for example, Gonzalez J. M. and Carlton B. C., 1982, Plasmid Transfer in *Bacillus thuringiensis*, 85–95, in Genetic and Cellular Technology, edited by L. P. Gage, Volume 1 Genetic Exchange, edited by U. N. Streips et al. Marcel Dekker, Inc. New York and Basel).

Conveniently, the conjugation is mediated by a conjugative plasmid. A suitable example of such conjugative plasmid is pAM$\beta$1 obtained from *Streptococcus faecalis*, generally known as $\beta$-plasmid. The latter is then introduced by known techniques (for example as disclosed by Fischer H.-M. 1983, Plasmid und Plasmidübertragung bei *Bacillus thuringiensis*, PHD Thesis ETH Nr. 7375, Swiss Federal Institute of Technology, ADAG Administration & Druck AG, 83 pages; or according to Gonzalez et al., as referred to hereinabove), into a B.t. strain. The thus obtained B.t. strain containing the $\beta$-plasmid, will then serve as donor in conjugation between the *kurstaki* and *tenebrionis* strain.

In order to facilitate detection and isolation of the conjugants (i.e. B.t. hybrid strains of the invention) both the donor and the recipient strain are marked genetically. Such markers can be introduced in a manner known per se. Thus, it is for example known, that in gramm-positive bacteria the $\beta$-plasmid confers resistance to erythromycin. This property can be used to eliminate all strains which, after conjugation, do not have this property.

When the other conjugation partner is also marked, e.g. by induced or spontaneous resistance to another antibiotic such as tetracycline, it will be possible to eliminate all those strains not having both genetic markers (i.e. all non-conjugated strains) by growing the microorganisms on adequate culture media containing erythromycin and tetracycline. The only organisms able to grow on such media will be those bearing both markers, i.e. the erythromycin resistance and the tetracycline resistance.

The final isolation of the B.t. hybrids of the invention may then be effected in a manner known per se, e.g. by visual identification of colonies containing crystal types of both B.t. *kurstaki* and B.t. *tenebrionis* strains, or by biological/biochemical techiques known in the art. A convenient procedure for the preparation of the B.t. hybrids of the invention is the conjugation of a B.t. *kurstaki* strain with a B.t. *tenebrionis* strain whereby the donor strain contains a conjugative plasmid and both the donor and recipient strains contain suitable selection genetic markers. In general, it will be preferred to use a B.t. *kurstaki* strain as a donor in the conjugation process of the invention.

In general, conjugation is suitably effected in a medium containing a nitrogen source, carbohydrates and growth factors at a temperature in the range of 20° to 40° C.

The starting materials may be obtained in conventional manner, starting from known B.t. *kurstaki* and B.t. *tenebrionis* strains.

The time of incubation is in general 4 to 96 hours, whereby for liquid media aeration or shaking is conveniently provided.

In the following, non-limting conjugation example, the B.t. *kurstaki* strain is used as a donor containing the $\beta$-plasmid serving as conjugative plasmid with a marker for erythromycin resistance. The recipient B.t. *tenebrionis* strain is a spontaeous tetracyclin-resistant mutant.

Temperatures are given in centigrade; parts are by weight.

EXAMPLE 1

Conjugation 2.5 ml of a culture of the B.t. *kurstaki* HD-73 (NRRL B-4488) strain containing the conjugative fragment pAM$\beta$1 of *Streptococcus faecalis* and 2.5 ml of a culture of a spontaneous tetracycline resistant mutant of B.t. *tenebrionis* (Deutsche Sammlung für Mikroorganismen, DSM 2803) - each in exponential growth phase (about $5 \times 10^7$ cells/mil) - are mixed, and filtered on a cellulose acetate membrane filter (Oxoid/Nuflow) (0.45 um, 25 mm diameter). The filter is laid on a Luria Medium (LA) plate (1 liter Luria Medium containing 15 g agar, 10 g tryptone, 5 g yeast extract, 10 g NaCl, 0.02 g thymidine in water) and incubated during 6 to 24 hours at 37°.

The filter is suspended in 0.5 ml of liquid LA (without Agar), vigorously homogenized and $10^0$ and $10^{-1}$ dilutions thereof are placed onto LA plates containing 50 ug/ml erythromycin and 5 ug/ml tetracycline to select the ex-conjugants.

The thus obtained erythromycin- and tetracycline resistent conjugants are placed on a medium allowing sporulation and then examined by microscope for the presence and the nature of delta-endotoxins: in hybrid strains, the sporangium contains, before lysis, a bi-pyramidal crystal typical for B.t. var. *kurstaki* strains, in addition to a parallellipipedic (or cubic) crystal typical for B.t. var. *tenebrionis* strains. Such crystals, having a size of approx. 2 um, are easily visible under the phase contrast microscope.

The hybrids are accordingly easily isolated by visual identification. The hybrid colonies (after 16 hours at 30° on LA plates) have the same morphology as B.t. *tenebrionis* colonies, but are easily distinguishable from the *kurstaki* colonies:

| Colonies | tenebrionis or hybrids | kurstaki |
| --- | --- | --- |
| Form | irregular | circular |

| Colonies | tenebrionis or hybrids | kurstaki |
| --- | --- | --- |
| Elevation | raised | convex |
| Margin | undulate | entire |
| Surface | rough | smooth |

The introduction of plasmids from the donor strain into the recipient strain may also be demonstrated physically by agarose gel electrophoresis analysis of the DNA extracted from the resulting hybrids. The DNA molecules (plasmids) are visualised by UV irradiation after ethidium bromide staining and photographed. (See Lereclus D., Menou G. and Lecadet M.-M., 1983, Mol. Gen. Genet. 191, 307-313).

Most hybrids of the invention possess, among others, the typical 10 Megadalton (Md) plasmid from the recipient B.t. *tenebrionis* strain and the 5.6 Md plasmid typical for the donor B.t. *kurstaki* strain. The plasmids bearing the gene coding for the delta-endotoxin in B.t. *kurstaki* and in B.t. *tenebrionis* have approximately the same molecular weight and are therefore not easily distinguishable in tne plasmidogram of the hybrid strain.

The B.t. hybrids of the invention have useful insecticidal properties. They are active against pests susceptible to B.t. *kurstaki* strains as well as against pests susceptible to B.t. *tenebrionis* strains. In general, they have insecticidal properties which are superior over those which are observed by physical mixture of the parent conjugation partners ("parents"), either in terms of level of insecticidal activity, or in terms of spectrum of activity, or both.

The surprising pesticidal properties of a selection of the B.t. hybrids of the invention are illustrated by their activity against the larva of *Trichoplusia ni* (cabbage looper), *Spodoptera littoralis* (Egyptian cotton leafworm) and *Phaedon cochleariae* (mustard beetle) in the following bioassay:

Bioassay

A $10^8$ spores/ml suspension in water is sprayed on medium-sized chinese cabbage leaves with a micro airbrush, up to run-off point. When the sprayed deposit is dry, each leaf is laid on a moist filter paper in a plastic petri dish of 9 cm diameter. 10 insects (2nd instar larvae) are introduced in each dish. 3 dishes are used per insect species.

The assay is performed in a climatic chamber at 25°, a relative humidity of 65% and a photoperiod of 16 hours.

Under these conditions the larvae are allowed to feed on the treated leaves during 5 days. Mortality among larvae is then estimated and expressed in %.

The results of the obtained are summarized in the following table.

| B.t. hybrid strain | % Mortality after 5 days | | |
| --- | --- | --- | --- |
| | Spodoptera | Trichoplusia | Phaedon |
| L21001 | 87 | 100 | 100 |
| L21004 | 90 | 100 | 100 |
| L21016 | 97 | 100 | 100 |
| L21017 | 97 | 100 | 100 |
| L21019 | 93 | 100 | 100 |
| kurstaki HD73[1] | 3 | 100 | 0 |
| tenebrionis[2] | 0 | 0 | 100 |
| tank mix "k + t"[3] | 0 | 100 | 43 |

[1]with β-plasmid (as used in conjugation example)
[2]tetracycline resistant strain (as used in conjugation example)
[3]mixture prepared just before spray application by suspending kurstaki[1] and tenebrionis[2] in equal proportions and adjusted to give a total concentration of $10^8$ spores/ml.

Some of the above hybrid strains have been deposited 15th Oct. 1985 with the Agricultural Research Culture Collection (NRRL), Peoria, Ill. 61604, U.S.A. Strains L2004, L21017 and L21019 have been assigned NRRL numbers B-18011, B-18012 and B-18013 resp.

The above tabulated data show that the hybrids L21001, L21004. L210016, L21017 and L21019 are not only active on insect species which are susceptible to their "parents" but, surprisingly, extend their activity to insect species, e.g. Spodoptera, which are not susceptible to the "parents". These results are particularly surprising, since the simple mixture of the "parents", is less active than *tenebrionis*, used alone, on Phaedon, and has no activity on Spodoptera.

The invention therefore also provides a method of combatting insects comprising applying to the insects or their habitat an insecticidally effective amount of a B.t. hybrid of the invention.

The B.t. hybrids of the invention are conveniently employed in insecticidal composition form, e.g. in suspension concentrate form or power form. Such compositions contain suitably diluents and preferably additional insecticidally acceptable additives such as UV protecting agents, surfactants, emulsifiers etc. They are prepared in conventional manner according to known B.t. strains containing biological insecticides.

The term diluents as used herein means liquid or solid, agriculturally acceptable material, which may be added to the B.t. hybrids of the invention to bring them in an easier or better applicable form, resp. to dilute the active agent to a usuable or desirable strength of activity.

It will be appreciated that the B.t. hybrids of the invention, once obtained by conjugation, will be more economically reproduced/multiplied by fermentation in an appropriate nutritive medium comprising a nitrogen source (e.g. fish meal), a carbohydrate source (e.g. starch) and mineral salts and adjusted to a pH of about 7.

Such fermentation is conveniently effected at a temperature of 20° to 40° C., e.g. 30° C. A suitable fermentation time is from 24 to 72 hours, e.g. 36 hours.

A suitable suspension concentrate of the B.t. hybrids of the invention can be obtained by evaporation of the fermentation liquor to the desired concentration. Additives may be added where desired..

Analogously, a wettable powder formulation may be obtained by spray drying the fermentation liquor, comprising optionally emulsifiers, UV protectants and the like, and pulverisation of the thus obtained solid.

The thus obtained formulations contain a substantial part of the components of the nutritive medium as diluent.

Alternatively, the fermentation liquor may be centrifugated to separate the bigger particles of the nutritive medium and then be converted, as indicated above, to a suitable suspension concentrate or wettable powder formulation. Suitable formulation comprise e.g. between 1.000 to 40.000 IU per mg or ml formulated product

Soluble Concentrate

An aqueous nutrient medium containing about 1.86% beet molasses, 1.4% oil-free cottonseed endosperm flour, 1.7% corn steep liquor solids and 0.1% calcium carbonate is formed, tne pH adjusted to within the range of 7.2 to 7.6 the batch sterilized for 20 to 30 minutes at 121° C. and then inoculated with 5% of its volume of a B.t. hybrid. The culturing process is run with agitation with about 5 psig back pressure and at an incubation temperature of 30° C. The broth is chilled to 18° to 20° C. and its pH adjusted to about 5.5 with concentrated $H_2SO_4$. The broth is screened through a screen having 150 meshes to the square inch, the resulting screened culture centrifuged to remove part of the impurities and evaporated to a concentrate volume having the desired potency. To this concentrate are added 0.4% by weight of an emulsifier(e.g. isooctyl phenyl polyoxyethanol) and 0.8% by weight of an UV absorber.

Wettable Powder

The evaporated concentrate volume obtained according to the preceding example is spray dried, and the thus obtained technical concentrate blended with a "carrier mixture" consisting of 10% silica and 90% soybean protein, the amount of carrier mixture depending on the potency of the technical concentrate and the desired potency of the wettable powder.

To this wettable powder may be added 0.4% by weight of an emulsifier and 0.8% by weight of a UV absorber.

Preferred B.t. hybrids of the invention are such obtainable by conjugation using B.t. *tenebrionis* as recipient strain and B.t. *kurstaki* as donor strain.

We claim:

1. Hybriid *Bacillus thuringiensis cells capble of producing delta-endotoxin crystals typical for Bacillus thuringiensis kurstaki,* also capable fo producing delta-endotoxin crystals typical for *Bacillus thuringiensis tenebrionis* and having insecticidal activity against the larvae of *trichoplusia ni, Spodoptera littoralis* and *Phaedon cochlaeriae*.

2. A hyrid in accord with claim 1 which is NRLL No. B-18011.

3. A hydrib in accord with claim 1 which is NRLL No. B-18012.

4. A hybrid in accord with claim 1 which is NRLL No. B-18013.

5. An insecticidal composition comprising an agriculturally acceptable diluent and an insecticidally effective amount of a B.t. hybrid of claim 1.

6. A composition in accord with claim 5 in which the B.t. hybrid is NRRL No. B-18011.

7. A composition in accord with claim 5 in which the B.t. hybrid is NRRL No. B-18012.

8. A composition in accord with claim 5 in which the B.t. hybrid is NRRL No. B-18013.

9. The method of combatting insects which comprises applying to the insects or their habitat an insecticidally effective amount of a B.t. hybrid of claim 1.

10. The method of claim 9 in which the B.t. hybric is NRRL No. B-18011.

11. The method of claim 9 in which the B.t. hybrid is NRRL No. B-18012.

12. The method of claim 9 in which the B.t. hybrid is NRRL No. B-18013.

* * * * *